United States Patent
Ashraf

[19]

[11] Patent Number: 5,951,580

[45] Date of Patent: Sep. 14, 1999

[54] SCALPEL HAVING TWO BLADES ADJUSTABLY SEPARABLE

[76] Inventor: Bahman Ashraf, 120 Wood Ave. South, Suite 305 Iselin, Iselin, N.J. 08830

[21] Appl. No.: 09/045,685

[22] Filed: Mar. 23, 1998

[51] Int. Cl.⁶ ............................................. A61B 17/32
[52] U.S. Cl. .................... 606/167; 606/168; 606/169; 606/170; 606/171; 30/272.1; 30/315
[58] Field of Search ................................ 606/167, 166, 606/168–185, 161, 131, 132, 137; 30/272.1, 315

[56] References Cited

U.S. PATENT DOCUMENTS

| | | | |
|---|---|---|---|
| 278,584 | 5/1883 | Moss | 30/315 |
| 5,100,391 | 3/1992 | Schutter et al. | 606/167 |
| 5,447,516 | 9/1995 | Gardner | 606/167 |

*Primary Examiner*—Michael Buiz
*Assistant Examiner*—Lien Ngo

[57] ABSTRACT

A scalpel is provided with horizontally separated first and second scalpel blades and with manually operated devices to adjust the separation between the blades as desired.

6 Claims, 1 Drawing Sheet

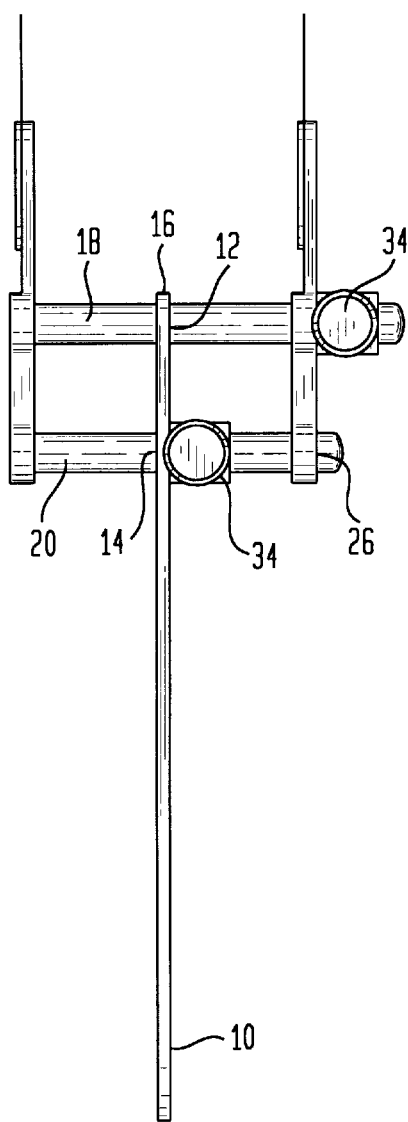
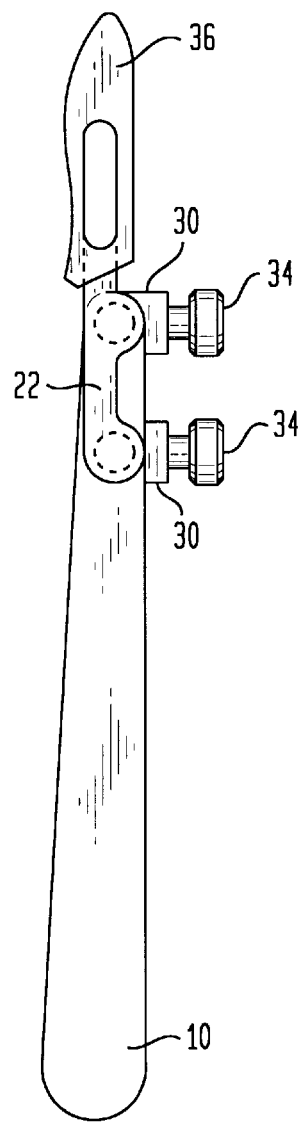
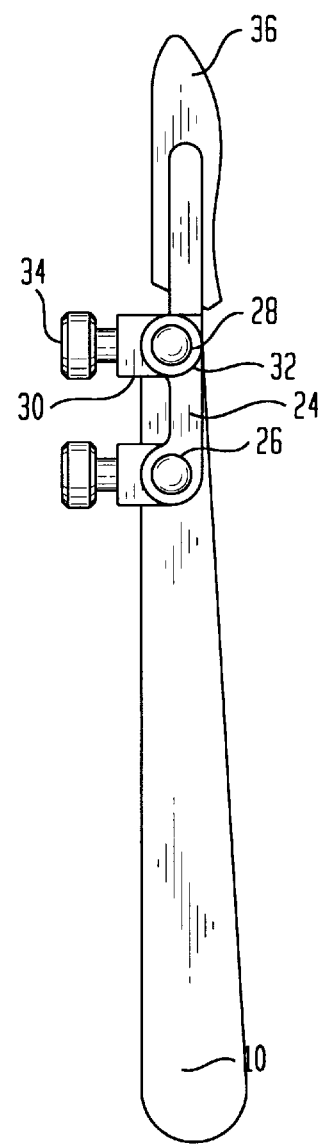
FIG. 1
FIG. 2
FIG. 3
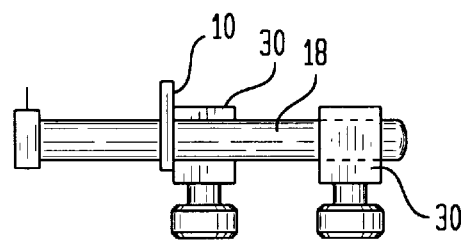
FIG. 4

SCALPEL HAVING TWO BLADES ADJUSTABLY SEPARABLE

BACKGROUND OF THE INVENTION

In various medical procedures it is necessary to remove strips of skin from a patient for skin grafts and the like. Originally, it was necessary for the physician removing such strips to make two separate spaced apart incisions. As such techniques were improved, double bladed scalpels were developed to enable the physician to make two spaced parallel incisions simultaneously. These scalpels contained the two blades in fixed relative position for producing strips of one fixed width. The present invention is directed toward a new and improved double bladed scalpel wherein the separation between the cutting edges of the blades can be adjusted manually for making incisions of different width.

SUMMARY OF THE INVENTION

Hence, it is an object of this invention to provide a new and improved double bladed scalpel wherein the separation between the cutting edges of the blades can be adjusted manually for making incisions of different width.

Another object is to provide a new and improved double bladed scalpel of the character indicated wherein the blades can be locked into desired positions and subsequently unlocked and set into different positions as required by the physician.

Yet another object is to provide a new and improved double bladed scalpel of the character indicated wherein the separation of the blades can be varied by the physician while making an incision so that a strip of skin having non parallel or irregular edges can be produced.

These and other objects and advanges of this invention will either be explained or will become apparent hereinafter.

In accordance with the principles of this invention, a scalpel having two blades adjustably separable employs an elongated handle having first and second transverse holes adjacent one end. These holes are spaced apart along the direction of elongation, the first hole being closer than the second hole to said one handle end. The handle has first and second opposite sides.

First and second parallel elongated members extend at right angles to the handle, each of the first and second members extending slidably through a corresponding one of the first and second holes. Each member has first and second opposite ends, the first ends of the first and second members being disposed along the first side of the handle, the second ends of the first and second members being disposed along the second side of the handle.

Third and fourth members are symmetrically disposed about the handle, each of the third and fourth members having rear and front ends. The third member is secured to said first ends of the first and second members with the rear end of the third member being secured to the first end of the second member. The fourth member has a first opening at its rear end through which the second end of the second member slidably extends with the rear ends of the third and fourth members being horizontally separated and horizontally aligned. The fourth member has a second opening through which the second end of the first member slidably extends.

First manually adjustable means is disposed slidably on the second member at a location intermediate its ends to adjust the horizontal separation between the rear ends of the third and fourth members to a desired value and to lock said third and fourth members in position while maintaining said symmetrical disposition about the handle.

Second manually adjustable means is slidably disposed on the second end of the first member to manually adjust the horizontal separation between the third and fourth members to said desired value and lock said third and fourth members in the adjusted position while maintaining these members symmetrically disposed about the handle.

In order to complete the scalpel, first and second scalpel blades are employed, each one of the blades being detachably secured to the first end of a corresponding one of the third and fourth members.

The adjustment of the horizontal separation between the third and fourth members sets the horizontal separation of the two blades. The scalpel can then be used in the manner explained above.

BRIEF DESCRIPTION OF THE DRAWINGS

FIG. 1 is a plan view of a preferred embodiment of the invention

FIG. 2 is a left side view thereof.

FIG. 3 is a right side view thereof.

FIG. 4 is a detail view of a portion of the structure of the preferred embodiment.

DETAILED DESCRIPTION OF PREFERRED EMBODIMENTS

Referring now to FIGS. 1–4, a scalpel having two blades adjustably separable employs a flat elongated surgical steel handle 10 having two opposite flat sides with first and second holes 12 and 14 extending transversely there through. Hole 12 is disposed at a front end 16 of the handle. Hole 14 is spaced therefrom, these holes being spaced apart along the axis of elongation.

First and second parallel elongated surgical steel bars or members 18 and 20 extend at right angles to the handle. The first member extends slidably through the first hole 12. The second member extends slidably through the second hole. Each of these members has first and second opposite ends, the first ends of the first and second members being disposed along the first side of the handle, the second ends of the first and second members being disposed along the second side of the handle.

Third and fourth parallel elongated surgical steel bars or members 22 and 24 of like length extend parallel to and being symmetrically disposed about the handle, each of the third and fourth members having rear and front ends. The third member 22 is permanently secured, as for example by silver soldering, to said first ends of the first and second members 18 and 20 with the rear end of the third member being secured to the first end of the second member 18.

The fourth member 24 has a first opening 26 at its rear end through which the second end of the second member 20 slidably extends. The rear ends of the third and fourth members are horizontally separated and horizontally aligned. The fourth member has a second opening 28 through which the second end of the first member slidably extends.

First manually adjustable means is disposed slidably on the second member intermediate its ends to adjust the horizontal separation between the rear ends of the third and fourth members to a desired value and lock said third and fourth members in position while maintaining said symmetrical disposition. This means takes the form of a surgical steel clip 30 having an opening 32 through which the second member extends so that the clip can be slid along the member to desired position and a surgical steel thumb screw 34 which can be manually tightened to lock the clip in desired position.

Second identical manually adjustable means is slidably disposed on the second end of the first member to manually adjust the horizontal separation between the third and fourth members to said desired value and lock said third and fourth members in the adjusted position while maintaining these members symmetrically disposed about the handle.

These two means maintain the third members in parallel alignment as well as enabling the user to lock these members with desired horizontal separation while the members remain symmetrically disposed about the handle.

Each one of two surgical scalpel blades or knives 36 slidably engages the front end of a corresponding one of the third and fourth members to complete the assembly of the scalpel.

While the invention has been described with particular emphasis on the drawings and descriptions thereof, the protection is limited only by the terms of the claims which follow.

What is claimed is:

1. A scalpel having two blades adjustably separable, said scalpel comprising:

an elongated handle having first and second transverse holes adjacent one end, the holes being spaced apart along the direction of elongation, the first hole being closer than the second hole to said one handle end, said handle having first and second opposite sides;

first and second parallel elongated members extending at right angles to the handle, each of the first and second members extending slidably through a corresponding one of the first and second holes, each member having first and second opposite ends, the first ends of the first and second members being disposed along the first side of the handle, the second ends of the first and second members being disposed along the second side of the handle;

third and fourth parallel elongated members of like length extending parallel to and being symmetrically disposed about the handle, each of the third and fourth members having rear and front ends, the third member being secured to said first ends of the first and second members with the rear end of the third member being secured to the first end of the second member;

the fourth member having a first opening at its rear end through which the second end of the second member slidably extends, the rear ends of the third and fourth members being horizontally separated and horizontally aligned, the fourth member having a second opening through which the second end of the first member slidably extends;

first manually adjustable means disposed slidably on the second member intermediate its ends to adjust the horizontal separation between the rear ends of the third and fourth members to a desired value and lock said third and fourth members in position while maintaining said symmetrical disposition; and second manually adjustable means slidably disposed on the second end of the first member to manually adjust the horizontal separation between the third and fourth members to said desired value and lock said third and fourth members in the adjusted position while maintaining these members symmetrically disposed about the handle.

2. The scalpel of claim 1 further including first and second scalpel knives, each knife being detachably secured to the front end of the corresponding one of the third and fourth members.

3. The scalpel of claim 2 wherein said handle has two opposite flat sides.

4. The scalpel of claim 3 wherein each manually adjustable means includes a clip having an opening through which the corresponding one of the first and second members can slide.

5. The scalpel of claim 4 wherein each clip has a manually adjustable thumb screw connected thereto for locking and unlocking the clip.

6. The scalpel of claim 5 wherein the members, handle, clips and thumbscrew are all composed of surgical steel.

\* \* \* \* \*